United States Patent
Hill (10) Patent No.: US 10,124,136 B2
(45) Date of Patent: Nov. 13, 2018

(54) DEVICES AND METHODS FOR DELIVERING AIR TO A PATIENT

(71) Applicant: Garland Hill, Hiawassee, GA (US)

(72) Inventor: Garland Hill, Hiawassee, GA (US)

(73) Assignee: Garland Hill, Hiawassee, GA (US)

( * ) Notice: Subject to any disclaimer, the term of this patent is extended or adjusted under 35 U.S.C. 154(b) by 224 days.

(21) Appl. No.: 15/361,706

(22) Filed: Nov. 28, 2016

(65) Prior Publication Data

US 2018/0147377 A1    May 31, 2018

(51) Int. Cl.
| | | |
|---|---|---|
| *A61M 16/00* | (2006.01) | |
| *A61M 16/12* | (2006.01) | |
| *A61M 16/08* | (2006.01) | |
| *A61M 16/06* | (2006.01) | |
| *A61M 16/10* | (2006.01) | |

(52) U.S. Cl.
CPC .... *A61M 16/0066* (2013.01); *A61M 16/0048* (2013.01); *A61M 16/0078* (2013.01); *A61M 16/0084* (2014.02); *A61M 16/06* (2013.01); *A61M 16/0816* (2013.01); *A61M 16/107* (2014.02); *A61M 16/125* (2014.02); *A61M 2202/0208* (2013.01)

(58) Field of Classification Search
CPC .......... A61M 16/0066; A61M 16/0084; A61M 16/107; A61M 16/125; A61M 16/0048; A61M 16/0078; A61M 16/06; A61M 16/0816; A61M 2202/0208
See application file for complete search history.

(56) References Cited

U.S. PATENT DOCUMENTS

| | | | |
|---|---|---|---|
| 2003/0168064 A1* | 9/2003 | Daly | A61M 16/0057 |
| | | | 128/204.18 |
| 2004/0020203 A1* | 2/2004 | Arnold | F01D 5/048 |
| | | | 60/602 |

* cited by examiner

*Primary Examiner* — Gregory Anderson
*Assistant Examiner* — Jonathan Paciorek
(74) *Attorney, Agent, or Firm* — Eversheds Sutherland (US) LLP

(57) ABSTRACT

Devices and methods for delivering air to a patient are provided. A device includes a first portion having a first airflow inlet and a first impeller configured to move in response to airflow from the first airflow inlet contacting the first impeller, the first portion defining a first airflow path; a second portion having a second airflow inlet, a second impeller, and an outlet for communicating airflow to a patient, the second portion defining a second airflow path; and means for coupling the first portion and the second portion, such that movement of the first impeller causes corresponding movement of the second impeller, wherein the second impeller is configured to impel air through the second airflow inlet and out of the outlet to the patient, upon movement of the second impeller and wherein the first and second airflow paths are not in fluid communication.

18 Claims, 8 Drawing Sheets

DEVICES AND METHODS FOR DELIVERING AIR TO A PATIENT

TECHNICAL FIELD

This disclosure relates generally to medical devices, and more particularly relates to devices and methods for delivering air to a patient.

BACKGROUND

Cardiopulmonary resuscitation (CPR) is an emergency medical procedure that traditionally combines chest compression with artificial ventilation in an effort to provide oxygenated blood through the body, and to the brain, in patients where a prolonged loss of circulation places the patient at risk. The rescuer may provide artificial ventilation by either exhaling air into the subject's mouth or nose (e.g., mouth-to-mouth resuscitation) or using a device that pushes air into the subject's lungs (e.g., mechanical ventilation). Mechanical ventilation typically involves a ventilator machine or a medical professional compressing a bag valve mask or a set of bellows. However, such mechanical ventilation equipment is typically available only in hospitals or ambulances and can be cumbersome to transport to patients in the field.

Thus, mouth-to-mouth resuscitation is typically used by medical personnel in the field to provide artificial ventilation to patients. However, mouth-to-mouth resuscitation significantly increases the risk of contamination between the patient and medical personnel due to the exhaled air from the medical personnel being inhaled by the patient. Moreover, because the exhaled air from the medical personnel contains increased carbon dioxide, as compared to atmospheric air, the patient receives less oxygen during mouth-to-mouth resuscitation than through typical breathing, at a time when oxygen intake is critical.

Thus, improved devices and methods for delivering air to a patient in need of artificial ventilation are needed.

SUMMARY

In one aspect, devices for delivering air to a patient are provided, including a first portion having a first airflow inlet and a first impeller configured to move in response to airflow from the first airflow inlet contacting the first impeller, the first portion defining a first airflow path; a second portion having a second airflow inlet, a second impeller, and an outlet for communicating airflow to a patient, the second portion defining a second airflow path; and means for coupling the first portion and the second portion, such that movement of the first impeller causes corresponding movement of the second impeller, wherein the second impeller is configured to impel air through the second airflow inlet and out of the outlet to the patient, upon movement of the second impeller, and wherein the first and second airflow paths are not in fluid communication.

In another aspect, methods for delivering air to a patient are provided, including providing a device that includes: a first portion having a first airflow inlet and a first impeller, the first portion defining a first airflow path; a second portion having a second airflow inlet, a second impeller, and an outlet for communicating airflow to a patient, the second portion defining a second airflow path; and means for coupling the first portion and the second portion, such that movement of the first impeller causes corresponding movement of the second impeller; providing air to the airflow inlet of the device to move the first impeller to cause movement of the second impeller, such that air is impelled through the second airflow inlet and out of the outlet to the patient, wherein the first and second airflow paths are not in fluid communication.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

DETAILED DESCRIPTION

Devices and methods for delivering air to patients are provided herein. In certain embodiments, these devices and methods provide improved delivery of oxygen to a patient in need of artificial ventilation.

In one aspect, as shown in FIGS. 1A-1B and 2A-2B, a device 100 for delivering air to a patient in need of artificial ventilation is provided. The device 100 includes a first portion 102 and a second portion 104. The first portion 102 has a first airflow inlet 106 and a first impeller 116 that is configured to move in response to airflow from the first airflow inlet 106 contacting the first impeller 116. The first portion 102 defines a first airflow path, including at least the first airflow inlet 106. In certain embodiments, the first airflow path further includes a first airflow outlet 108. The second portion 104 has a second airflow inlet 110, a second impeller 118, and a second airflow outlet 112 for communicating airflow to the patient. The second portion 104 defines a second airflow path, including at least the second airflow inlet 110 and the second airflow outlet 112. The device 100 further includes means for coupling the first portion 102 and the second portion 104, such that rotational movement of the first impeller 116 drives corresponding rotational movement of the second impeller 118. The second impeller 118 is configured to impel air through the second airflow inlet 110 and out of the second airflow outlet 112 to the patient, upon movement of the second impeller 118. In certain embodiments, the first and second airflow paths are substantially not in fluid communication.

Thus, the device 100 is configured such that a user can exhale, or otherwise provide air, into the first airflow inlet 106 to effectuate movement of the second impeller 118 that impels air from the surrounding atmosphere through the second portion 104 of the device and out through the second airflow outlet 112 to the patient. Moreover, because the airflow paths may not be in fluid communication (i.e., are not directly connected), the risk of contamination from the user to the patient is minimized, as the exhaled air is not provided directly to the patient. Instead, air from the atmosphere (which contains a higher volume of oxygen than exhaled air) is provided to the patient.

Figure 1A:
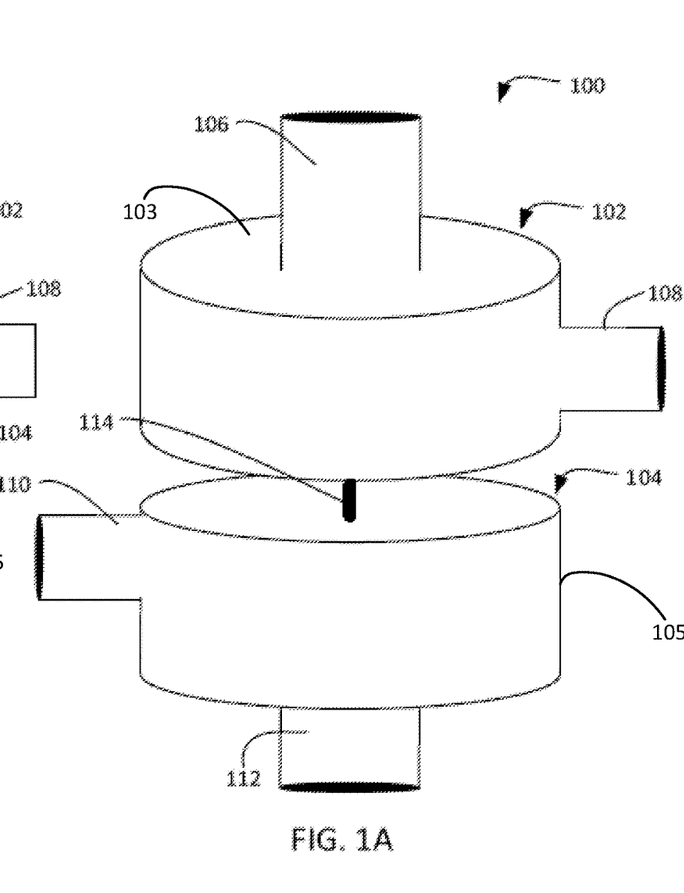
FIGS. 1A and 1B are a perspective view and a cross-sectional view, respectively, of an embodiment of a device for delivering air to a patient, in accordance with the present disclosure.
Figure 1B:
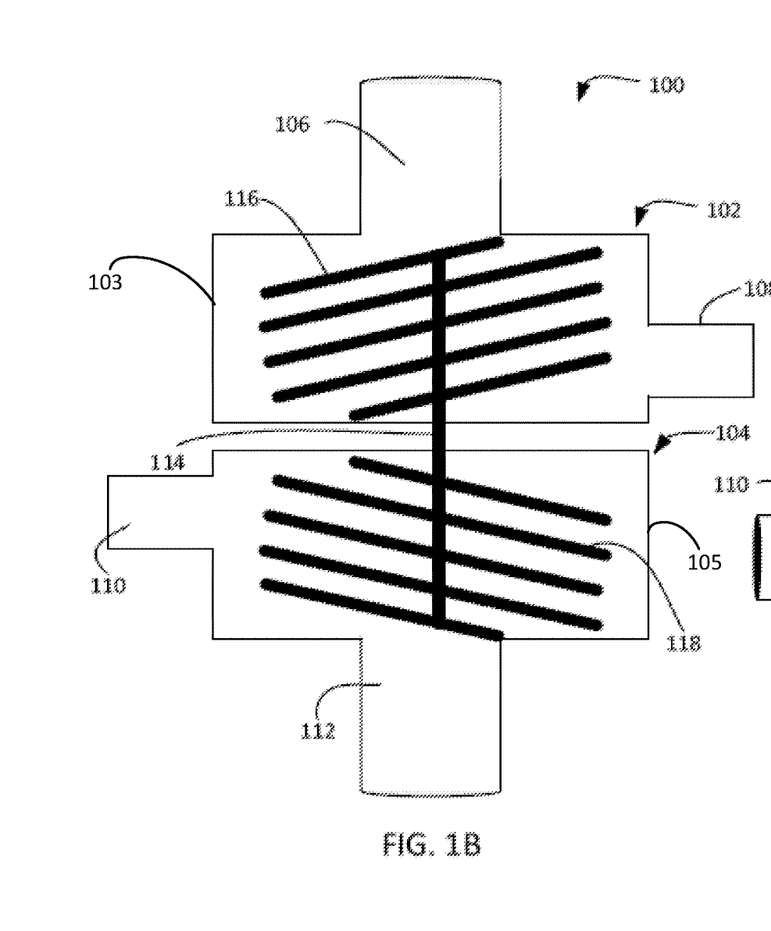
Figure 2A:
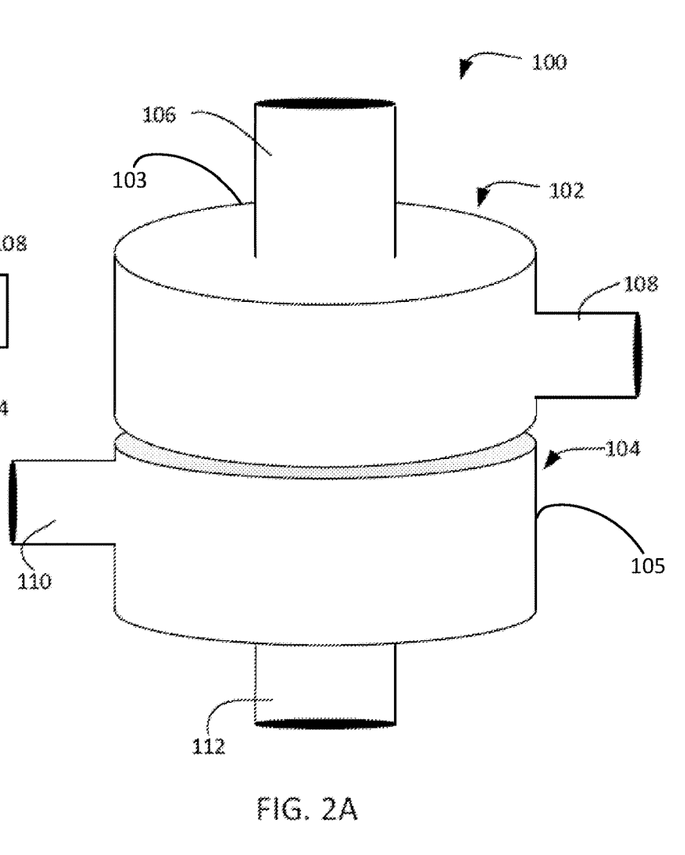
FIGS. 2A and 2B are a perspective view and a cross-sectional view, respectively, of an embodiment of a device for delivering air to a patient, in accordance with the present disclosure.
Figure 2B:
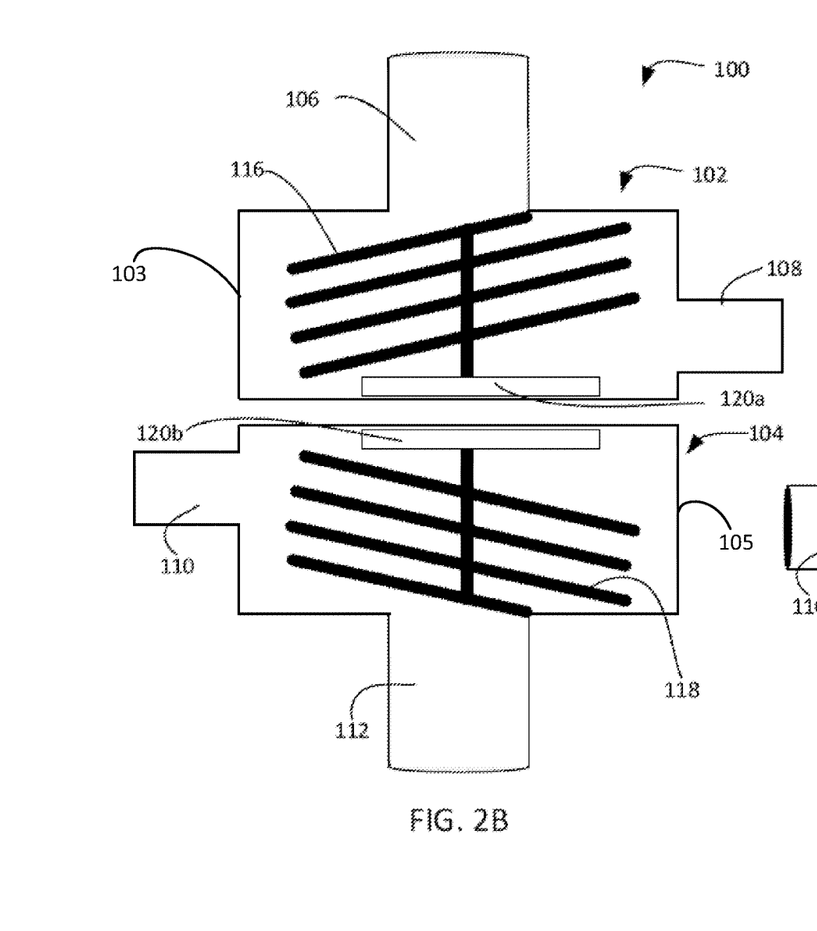

The means for coupling the first portion 102 and the second portion 104 may be any suitable means which would be understood by one of ordinary skill in the art, including various mechanical couplings. As used herein, the term "couples" and "coupling" are used broadly and refers to components being directly or indirectly connected to one another via any suitable fastening, connection, or attachment mechanism. In some embodiments, as shown in FIGS. 1A and 1B, the means for coupling the first portion 102 and the second portion 104 includes a mechanical coupling 114 of the first impeller 116 and the second impeller 118. For example, the mechanical coupling may be a shaft 114 that couples the first impeller 116 and the second impeller 118. In certain embodiments, the shaft of the mechanical coupling may be sealed, such that the first and second airflow paths are not in fluid communication. For example, the shaft may be coated with a lubricious substance that permits movement of the shaft while sealing the shaft. In another example, an elastomeric gasket, such as a rubber gasket, may be provided to seal the opening(s) between the shared shaft and the wall(s) defining the housings of the two portions 102, 104. In other embodiments, as shown in FIGS. 2A and 2B, the means for coupling the first portion and the second portion includes a magnetic connection 120a, 120b between the first impeller 116 and the second impeller 118, such that movement of the first impeller 116 causes corresponding movement of the second impeller 118. Any suitable configuration of a magnetic connection may be used. A magnetic connection beneficially may eliminate openings in the first and second portions 102, 104, other than those defining the airflow paths.

As shown in FIGS. 1A-1B, 2A-2B, and 3, the first and second portions 102, 104 may each include a housing 103, 105 that contains the impeller 116, 118, and defines the airflow inlet/outlet 106, 108, 110, 112. The housings 103, 105 of the first and second portions 102, 104 may be integrally or separately formed. That is, the housings 103, 105 of the first and second portions 102, 104 may share one or more common walls or may be wholly separate from one another. The housings 103, 105 illustrated in FIGS. 1A-1B and 2A-2B are separate housings that are generally cylindrical in shape; however, it should be understood that any suitable size and shape of the housings may be employed.

Figure 7:
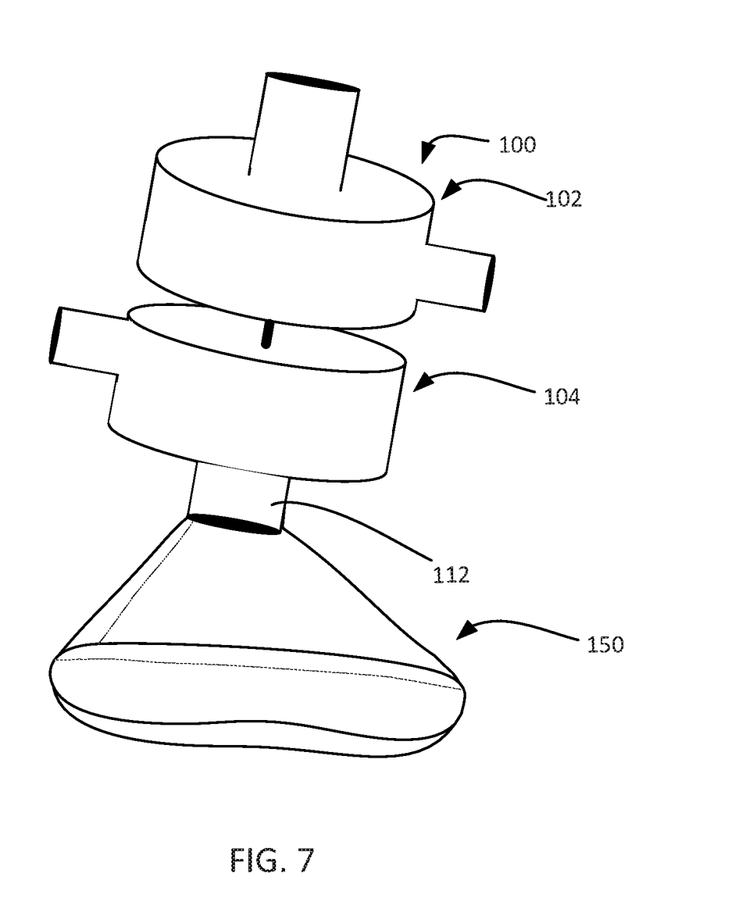
FIG. 7 is a perspective view of an embodiment of a device for delivering air to a patient coupled to a respiratory mask, in accordance with the present disclosure.
Figure 8:
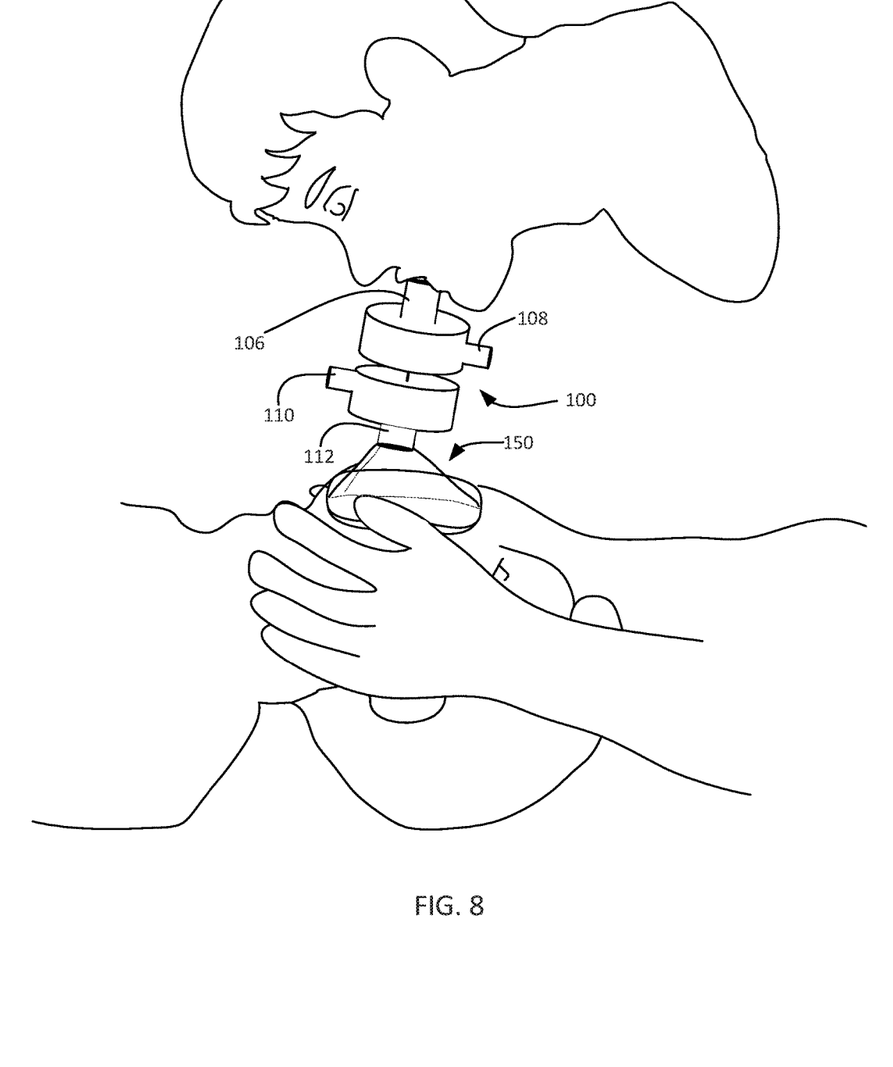
FIG. 8 is a perspective view of an embodiment of a device for delivering air to a patient coupled to a respiratory mask, in use, in accordance with the present disclosure.
Figure 9:
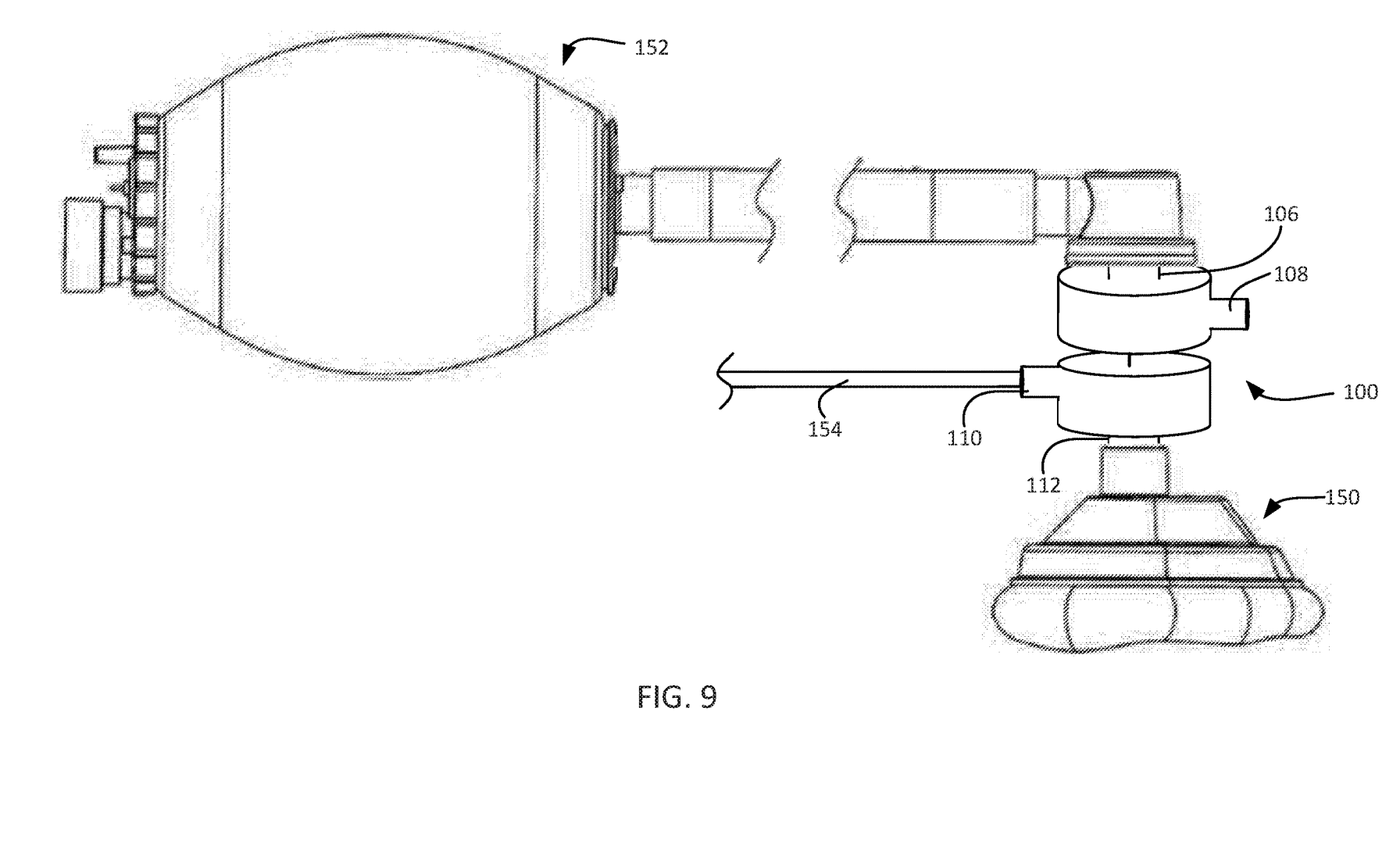
FIG. 9 is a perspective view of an embodiment of a device for delivering air to a patient coupled to a respiratory mask, an oxygen tank connector, and a bag valve mask, in accordance with the present disclosure.
Figure 10:
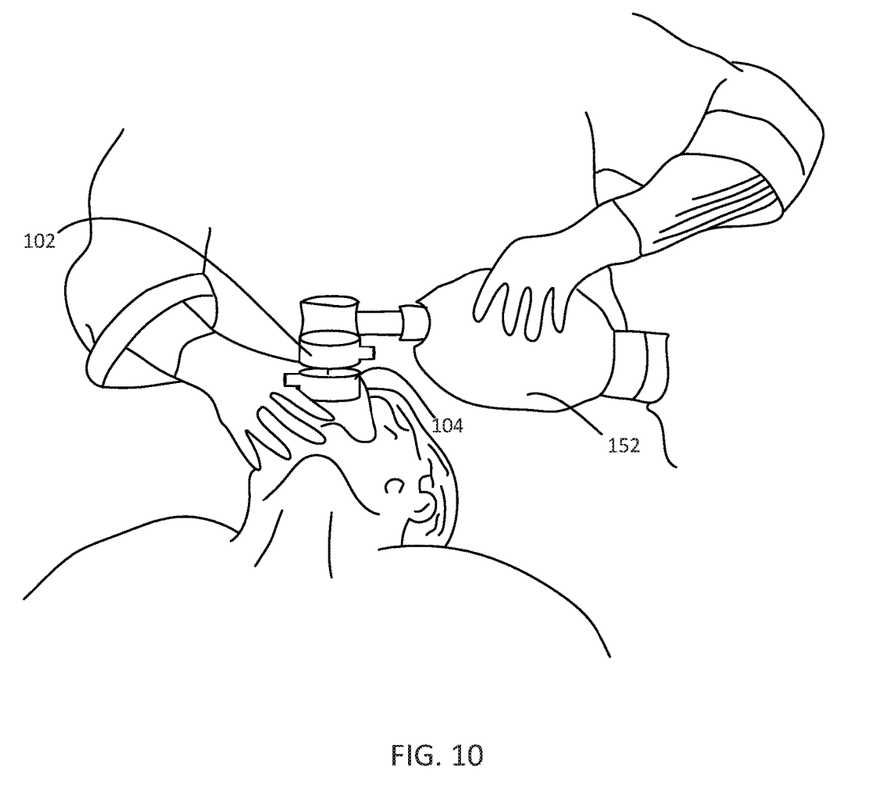
FIG. 10 is a perspective view of an embodiment of a device for delivering air to a patient coupled to a respiratory mask, and a bag valve mask, in use, in accordance with the present disclosure.

The airflow inlets and outlets may be formed integrally with or coupled to the housings of the first and second portions. The airflow inlets and outlets may have any suitable size and shape. For example, the inlets and outlets may be provided in the form of spouts, tubes, openings, vents, channels, or other suitable configurations. Additionally, the inlets and outlets may optionally include threads, flanges, or other suitable attachment means for coupling the inlet or outlet to an external apparatus, such as an bag valve mask 152 (as shown in FIGS. 9 and 10), a respiratory mask 150 (as shown in FIGS. 7 and 8), and/or an oxygen tank connector 154 (as shown in FIG. 9). For example, the second airflow outlet 112 of the second portion 104 of the device 100 may be configured for coupling to a respiratory mask 150 or pocket ventilator that is configured to fit over a patient's mouth. For example, the first airflow inlet 106 of the first portion 102 of the device 100 may be configured for coupling to a mechanically driven air source, such as a bag valve 152. For example, the second airflow inlet 110 of the second portion 104 of the device 100 may be configured for coupling to an oxygen tank, such as via oxygen tube 154. In other embodiments, the second airflow inlet 110 is open to the atmosphere.

In some embodiments, the second portion 104 contains a filter configured to filter air impelled through the second airflow inlet. For example, the filter may be a screen or mesh, or a porous material designed to trap entrained particulate matter, keeping it from being introduced into the patient's lungs.

Thus, in use, a rescuer may exhale air or squeeze a bag mask to propel air through the first airflow path of the first portion 102 of the device 100. This exhaled air in turn rotates or otherwise imparts motion to the first impeller 116, which translates into motion of the second impeller 118. Motion of the second impeller results in air from the attached air source (e.g., atmosphere or another oxygen supply) being pulled into the second portion 104 and expelled from the outlet 112, and into an attached mask or patient mouth.

Figure 3:
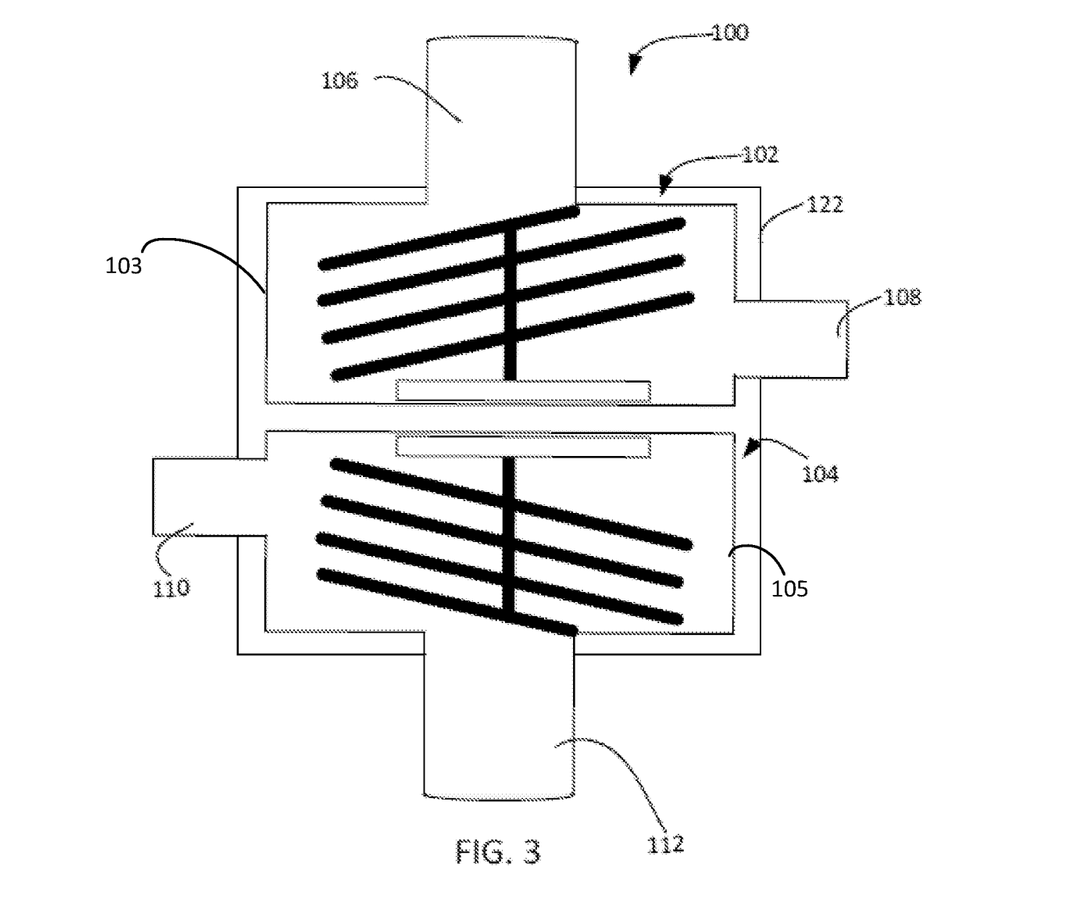
FIG. 3 is a cross-sectional view of an embodiment of a device for delivering air to a patient, in accordance with the present disclosure.
Figure 4A:
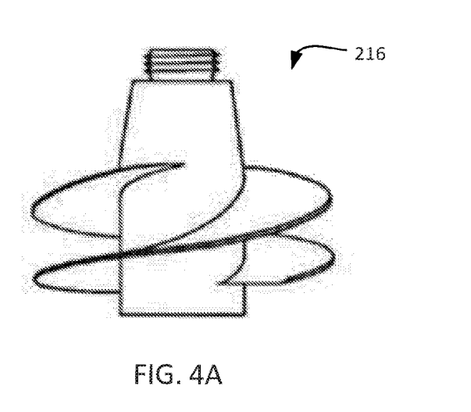
FIGS. 4A and 4B are a perspective view and an upper plan view, respectively, of an embodiment of an impeller, in accordance with the present disclosure.
Figure 4B:
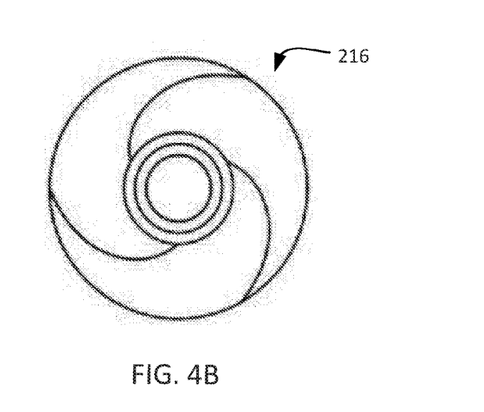
Figure 5A:
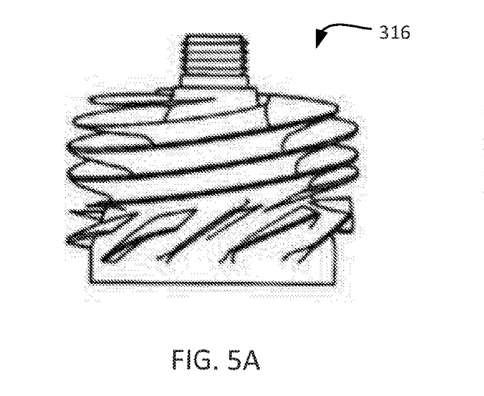
FIGS. 5A and 5B are a perspective view and an upper plan view, respectively, of an embodiment of an impeller, in accordance with the present disclosure.
Figure 5B:
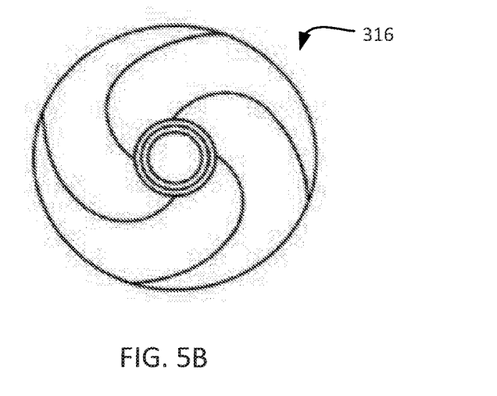
Figure 6A:
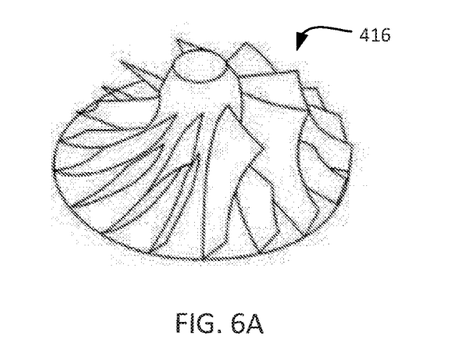
FIGS. 6A and 6B are a perspective view and an upper plan view, respectively, of an embodiment of an impeller, in accordance with the present disclosure.
Figure 6B:
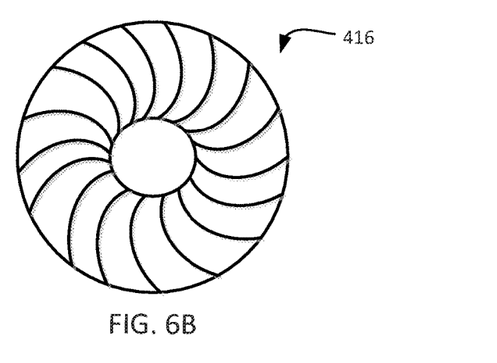

In the embodiments shown in FIGS. 1A-1B and 2A-2B, the housing 103 for the first portion 102 is generally cylindrical in shape, and the housing 105 for the second portion 104 is generally cylindrical in shape, with the first airflow inlet 106 and the second airflow outlet 112 being disposed on opposed external faces of the cylindrical housings 103, 105. The faces of each cylindrical housings 103, 105 opposite the airflow inlet 106 or the airflow outlet 112 are positioned in a facing relationship. As shown in FIGS. 1A-1B and 2A-2B, the first airflow inlet 106 and the second airflow outlet 112 may be disposed substantially along a central, longitudinal axis of the device. As shown in FIGS. 1A-1B and 2A-2B, the first airflow outlet 108 and the second airflow inlet 110 may be disposed in the sidewall of the housing 103, 105. However, it should be understood that the various airflow outlets and inlets may be disposed at any suitable location or sidewall/end wall of the device. In some embodiments, as shown in FIG. 3, the first portion 102 and the second portion 104 are contained within a common housing 122. For example, the first and second portions 102, 104 may be defined by a common housing and separated by a wall interposed between the impellers 116, 118.

Any suitable impeller (e.g., rotor) designs may be used in the present devices 100. For example, in the first portion 102, any suitable impeller 116 that is capable of rotation or other movement in response to an airflow traveling across or around the impeller 116 may be used. For example, in the second portion 104, any suitable impeller 118 that is capable of pulling in or impelling air through the second airflow path upon rotation or other movement of the impeller 118 may be used. For example, various impeller designs are shown at FIGS. 4A-4B, 5A-5B, and 6A-6B. Impellers having various fin designs, such as impellers 216, 316, and 416 may be used in the presently described devices 100. The fins of the first impeller 116 may be angled or otherwise configured to achieve the desired movement in response to air traveling thereacross, while the fins of the second impeller 118 may be angled or otherwise configured to achieve the desired inflow of air in response to movement of the second impeller 118.

The components of the devices 100 described herein may be formed from any suitable materials or combination of materials. For example, the housings, impellers, and mechanical coupling may be formed from suitable materials such as plastics and metals. In certain embodiments, the device 100 is configured for one-time, disposable use. In other embodiments, the device 100 is configured to be reusable and can be sanitized without harming the device components.

In other aspects, methods for delivering air to a patient are provided. For example, the methods may include providing air to the airflow inlet of a device 100 having any configuration described herein to move the first impeller to cause movement of the second impeller, such that air is impelled through the second airflow inlet and out of the outlet to the patient. For example, as shown in FIG. 10, the air may be provided to the first airflow inlet of the device via a mechanically driven air source 152 coupled to the first airflow inlet of the first portion 102. For example, as shown in FIG. 9, the air may be impelled through the second airflow inlet 110 from an oxygen tank coupled to the second airflow inlet 110, such as via tube 154.

In further aspects, kits are provided, including a device 100 having any configuration described herein and a respiratory mask 150 configured for attachment to the outlet of the second portion 112 of the device 100.

Thus, the presently described devices and methods beneficially provide air to a patient via a rescuer exhaling (or pumping a bag valve, etc.), while reducing the risk of contamination between the patient and rescuer, due to the exhaled air from the medical personnel being directed away from the patient, while clean air from the atmosphere or another oxygen supply is inhaled by the patient. Because the exhaled air from the rescuer contains increased carbon dioxide, as compared to atmospheric air, the patient receives more oxygen than as compared to during mouth-to-mouth resuscitation, at a time when oxygen intake is critical. Moreover, the barrier between the two portions of the device (i.e., the portion that the rescuer contacts and the portion that the patient contacts) limits the potential exposure of the rescuer to regurgitation from the patient.

Further, the device of the present disclosure is compact and simple to use, such that it may be easily transported by medical personnel into the field and/or may be provided at first aid stations/kits at various locations, such as at emergency stations in workplaces.

While the disclosure has been described with reference to a number of example embodiments, it will be understood by those skilled in the art that the disclosure is not limited to such disclosed embodiments. Rather, the disclosed embodiments can be modified to incorporate any number of variations, alterations, substitutions, or equivalent arrangements not described herein, but which are commensurate with the spirit and scope of the disclosure.

I claim:

1. A device for delivering air to a patient, comprising:
   a first portion comprising a first airflow inlet and a first impeller configured to move in response to airflow from the first airflow inlet contacting the first impeller, the first portion defining a first airflow path;
   a second portion comprising a second airflow inlet, a second impeller, and an outlet for communicating airflow to a patient, the second portion defining a second airflow path; and
   means for coupling the first portion and the second portion, such that movement of the first impeller causes corresponding movement of the second impeller,
   wherein the second impeller is configured to impel air through the second airflow inlet and out of the outlet to the patient, upon movement of the second impeller,
   wherein the first and second airflow paths are not in fluid communication,
   wherein the outlet is configured for coupling to a respiratory mask or to fit over the patient's mouth.

2. The device of claim 1, wherein the means for coupling the first portion and the second portion comprises a mechanical coupling of the first impeller and the second impeller.

3. The device of claim 2, wherein the mechanical coupling comprises a shaft coupling the first impeller to the second impeller.

4. The device of claim 3, wherein the shaft is sealed, such that the first and second airflow paths are not in fluid communication.

5. The device of claim 4, wherein the shaft is coated with a lubricious substance that permits movement of the shaft while sealing the shaft.

6. The device of claim 1, wherein the means for coupling the first portion and the second portion comprises a magnetic connection between the first impeller and the second impeller, such that movement of the first impeller causes corresponding movement of the second impeller.

7. The device of claim 1, wherein the first airflow inlet is configured for coupling to a mechanically driven air source.

8. The device of claim 1, wherein the second airflow inlet is configured for coupling to an oxygen tank.

9. The device of claim 1, wherein the second portion further comprises a filter configured to filter air impelled through the second airflow inlet.

10. A method for delivering air to a patient, comprising:
    providing a device that comprises:
      a first portion comprising a first airflow inlet and a first impeller, the first portion defining a first airflow path;
      a second portion comprising a second airflow inlet, a second impeller, and an outlet for communicating airflow to a patient, the second portion defining a second airflow path; and
      means for coupling the first portion and the second portion, such that movement of the first impeller causes corresponding movement of the second impeller;
    providing air to the airflow inlet of the device to move the first impeller to cause movement of the second impeller, such that air is impelled through the second airflow inlet and out of the outlet to the patient,
    wherein the first and second airflow paths are not in fluid communication,
    wherein the outlet is configured for coupling to a respiratory mask or to fit over the patient's mouth.

11. The method of claim 10, wherein the air is provided to the first airflow inlet of the device via a mechanically driven air source coupled to the first airflow inlet.

12. The method of claim 10, wherein the air is impelled through the second airflow inlet from an oxygen tank coupled to the second airflow inlet.

13. The method of claim 10, wherein the means for coupling the first portion and the second portion comprises a mechanical coupling of the first impeller and the second impeller.

14. The method of claim 13, wherein the mechanical coupling comprises a shaft coupling the first impeller to the second impeller.

15. The method of claim 14, wherein the shaft is sealed, such that the first and second airflow paths are not in fluid communication.

16. The method of claim 10, wherein the means for coupling the first portion and the second portion comprises a magnetic connection between the first impeller and the second impeller, such that movement of the first impeller causes corresponding movement of the second impeller.

17. The method of claim 10, wherein the second portion further comprises a filter configured to filter air impelled through the second airflow inlet.

18. A kit comprising:
   the device of claim 1, and
   a respiratory mask configured for attachment to the outlet of the second portion of the device.

* * * * *